United States Patent [19]
Denis et al.

[11] Patent Number: 5,227,522
[45] Date of Patent: Jul. 13, 1993

[54] PREPARATION OF ADIPIC ACID BY HYDROCARBOXYLATION OF PENTENIC ACIDS

[75] Inventors: Philippe Denis, Decines; Jean-Michel Grosselin, Francheville; Francois Metz, Vernaison, all of France

[73] Assignee: Rhone-Poulenc Chimie, Courbevoie, France

[21] Appl. No.: 873,095

[22] Filed: Apr. 24, 1992

[30] Foreign Application Priority Data

Apr. 26, 1991 [FR] France ................................. 91 05542

[51] Int. Cl.$^5$ .............................................. C07C 51/14
[52] U.S. Cl. .................................................... 562/522
[58] Field of Search ................................. 562/522, 517

[56] References Cited

U.S. PATENT DOCUMENTS

| | | | |
|---|---|---|---|
| 3,816,489 | 6/1974 | Craddock et al. | 260/413 |
| 4,861,912 | 8/1989 | Drent et al. | 562/522 X |
| 4,902,822 | 2/1990 | Drent | 562/522 X |
| 5,028,576 | 7/1991 | Drent et al. | 562/522 X |

OTHER PUBLICATIONS

D. Forster et al, "Mechanistic Pathways in the Catalysis of Olefin Hydrocarboxylation by Rhodium, Iridium, and Cobalt Complexes", *Catalysis Reviews*, vol. 23, Nos. 1 and 2 (1981), pp. 89–105.

*Primary Examiner*—Arthur C. Prescott
*Attorney, Agent, or Firm*—Burns, Doane, Swecker & Mathis

[57] ABSTRACT

Adipic acid is selectively prepared by reacting water and carbon monoxide with at least one pentenic acid, in the presence of an iridium-based catalyst and at least one iodine-containing promoter therefor, at an elevated temperature, at a pressure greater than atmospheric pressure, in a reaction medium comprising at least one saturated aliphatic carboxylic acid, ethylenically unsaturated aliphatic carboxylic acid or aromatic carboxylic acid having not more than 20 carbon atoms, with the I/Ir atomic ratio being less than 10.

16 Claims, No Drawings

PREPARATION OF ADIPIC ACID BY HYDROCARBOXYLATION OF PENTENIC ACIDS

BACKGROUND OF THE INVENTION

1. Field of the Invention

The present invention relates to the preparation of adipic acid by hydrocarboxylation of pentenic acids, and, more especially, to the preparation of adipic acid by reacting water and carbon monoxide with at least one pentenic acid.

2. Description of the Prior Art

U.S. Pat. No. 3,579,551 describes a process for the preparation of carboxylic acids by reacting ethylenically unsaturated compounds with carbon monoxide and water, in the presence of a catalyst composition essentially consisting of iridium compounds or complexes and an iodine-containing promoter. The ethylenically unsaturated compounds are selectively converted into carboxylic (linear and branched) acids by the subject reaction, preferably conducted in liquid phase, at a temperature ranging from 50° to 300° C. (preferably from 125° to 225° C.) and at partial carbon monoxide pressures advantageously ranging from 5 to 3,000 p.s.i.a. or even from 25 to 1,000 p.s.i.a.

It appears that any source of iridium can be employed, and various sources of iodine-containing promoters are indicated; the I/Ir atomic ratio can vary over wide limits (1:1 to 2,500:1) and preferably from 3:1 to 300:1.

The liquid reaction mixture may contain any solvent which is compatible with the catalyst system, $C_2$–$C_{20}$ monocarboxylic acids being the preferred solvents.

Example 1 of this '551 patent, carried out using propylene as a starting material, indicates that such a system promotes the formation of branched carboxylic acids (isobutyric).

Example 19 thereof, carried out using 1-hexene as a starting material, confirms the high proportion of branched carboxylic acids thus obtained.

Such a disadvantage (lack of selectivity for linear carboxylic acids) is addressed by U.S. Pat. No. 3,816,489, describing conducting the reaction in question with an I/Ir atomic ratio ranging from 3:1 to 100:1 to obtain predominantly terminal carboxylic acids.

While the fundamental advantage of the above techniques is undisputed in the case of raw materials comprising nonfunctionalized olefinically unsaturated compounds, and in particular in the case of olefins, per se, the adaptation of such techniques to starting materials which, in addition to the site of ethylenic unsaturation, contain a functional group which is reactive under the conditions of the subject reaction, presents many difficulties.

In particular, it has been determined that adaptations conducted using pentenic acids result in at least partial failure, since competing reactions other than that specifically desired occur to the detriment or even complete replacement of the latter, because of the presence of a —COOH functional group on the ethylenically unsaturated starting material compound.

Thus, serious need exists in this art for such a process that simultaneously provides good performance in respect of the carbonylation reaction and an appreciable selectivity for adipic acid.

SUMMARY OF THE INVENTION

Accordingly, a major object of the present invention is the provision of an improved process for the preparation of adipic acid, comprising reacting water and carbon monoxide with at least one pentenic acid, in the presence of an iridium-based catalyst and of at least one iodine-containing promoter therefor, at an elevated temperature, at a pressure greater than atmospheric pressure, in at least one carboxylic acid selected from among saturated aliphatic carboxylic acids, ethylenically unsaturated aliphatic carboxylic acids and aromatic carboxylic acids having not more than 20 carbon atoms, with the I/Ir atomic ratio being less than 10.

DETAILED DESCRIPTION OF THE PREFERRED EMBODIMENTS OF THE INVENTION

More particularly according to the present invention, by "pentenic acid" are intended 2-pentenoic acid, 3-pentenoic acid, 4-pentenoic acid and mixtures thereof.

4-Pentenoic acid provides good results but is not readily available.

3-Pentenoic acid, either alone or mixed with its isomers, is more particularly suitable by reason of its availability and of the satisfactory results which it provides.

The process according to the present invention requires the presence of an iridium-based catalyst. Any source of iridium can be used. Exemplary such sources of iridium include:

Metallic Ir, $IrO_2$, $Ir_2O_3$, $IrCl_3$, $IrCl_3.H_2O_3$, $IrBr_3$, $IrBr_3 3H_2O$, $IrI_3$, $Ir_2(CO)_4Cl_2$, $Ir_2(CO)_4I_2$, $Ir_2(CO)_8$, $Ir_4(CO)_{12}$, $Ir_2(CO)[P(C_6H_5)_3]_2I$, $Ir(CO)[P(C_6H_5)_3]_2Cl$, $Ir[P(C_6H_5)_3]_3I$, $HIr[P(C_6H_5)_3]_3(CO)$, $Ir(acac)(CO)_2$ $[IrCl(Cod)]_2$ (Cod: 1,5-cyclooctadiene, acac: acetylacetonate).

More particularly suited for carrying out the subject process are $[IrCl(Cod)]_2$, $Ir_4(CO)_{12}$ and $Ir(acac)(CO)_2$.

The amount of iridium to be used can vary over wide limits.

In general, an amount, expressed in moles of metallic iridium per liter of reaction mixture, ranging from $10^{-4}$ to $10^{-1}$ provides satisfactory results. Smaller amounts may be used; it is observed, however, that the reaction rate is low. Larger amounts present no disadvantages other than economic restraints.

The iridium concentration preferably ranges from $5 \times 10^{-4}$ to $10^{-2}$ mol/l, inclusive.

By "iodine-containing promoter" are intended HI and the organic iodine compounds capable of generating HI under the conditions of reaction and, in particular, $C_1$-$C_{10}$ alkyl iodides, with methyl iodide being more particularly preferred.

An essential parameter of the process of the invention is that the quantity of iodine-containing promoter to be used is such that the I/Ir molar ratio is less than 10. It is desirable that this ratio be higher than or equal to 0.1. The I/Ir molar ratio preferably ranges from 1 to 5, inclusive.

The presence of water is required to carry out the process according to the present invention. The quantity of water to be used is typically such that the water/pentenic acid(s) molar ratio ranges from 0.01 to 10, inclusive.

A larger amount is not desirable because of the loss in catalyst activity which is observed. The water/pentenic acid(s) molar ratio in the reaction mixture can be momentarily less than the minimum value indicated above if the process is carried out, for example, employing continuous water injection, rather than it being introduced with the other starting material charges prior to the hydrocarboxylation reaction.

The water/pentenic acid(s) molar ratio preferably ranges from 0.01 to 1, inclusive, the above comment concerning the minimum value also being applicable here.

Another essential parameter of the process of the present invention is that the reaction be carried out in at least one carboxylic acid reaction medium selected from among the saturated aliphatic carboxylic acids, ethylenically unsaturated aliphatic carboxylic acids and aromatic carboxylic acids having not more than 20 carbon atoms.

The precise nature of the carboxylic acid is not critical, provided that this acid is in the liquid state under the reaction conditions.

Exemplary such carboxylic acids include:

Acetic acid, propionic acid, butyric acid, valeric acid, adipic acid, 2-pentenoic acid, 3-pentenoic acid, 4-pentenoic acid, mixtures of two or three of the above pentenic acids, benzoic acid and phenylacetic acid.

A $C_2$-$C_8$ saturated aliphatic carboxylic acid is preferably used. Acetic acid is more particularly preferred according to the present invention. Adipic acid, the preparation of which is the focus of the invention, is also suitable.

In another preferred embodiment of the invention, 2-pentenoic acid, 3-pentenoic acid, 4-pentenoic acid and various mixtures of these acids are employed as the carboxylic acids.

The amount of carboxylic acid present in the reaction mixture may vary over wide limits, for example from 10% to 99%, inclusive, by volume of the reaction mixture. This amount preferably ranges from 30% to 99% by volume, inclusive. When the carboxylic acid employed is selected from among the pentenic acids, the upper limits of the values indicated above are the regions of choice.

As indicated above, the reaction is conducted at a pressure above atmospheric pressure and in the presence of carbon monoxide.

Substantially pure or technical grade carbon monoxide, as is available commercially, is well suited.

The reaction is preferably carried out in the liquid phase, it being possible for the total pressure to vary over wide limits and the reaction temperature generally ranging from 100° to 240° C. and preferably from 160° to 190° C.

The partial pressure of the carbon monoxide typically ranges from 2 to 250 bars and to advantageously carry out the process according to the invention it will range from 5 to 10 bars.

The reaction mixture contains the saturated aliphatic carboxylic acid, the ethylenically unsaturated aliphatic carboxylic acid or the aromatic carboxylic acid, water, one or more sources of iridium, one or more iodine-containing promoters and, if appropriate, all or a fraction of the pentenic acid(s) used and reaction products.

At the end of the reaction or of the time allocated thereto, the adipic acid is separated off by any suitable means, for example by crystallization and/or distillation of the carboxylic acid.

In order to further illustrate the present invention and the advantages thereof, the following specific examples are given, it being understood that same are intended only as illustrative and in nowise limitative.

EXAMPLE 1

The following materials were introduced into a glass ampoule purged beforehand with argon:

| | |
|---|---|
| (i) | 33.6 mg (0.1 mmol) of iridium in the form of [IrCl(Cod)]$_2$; |
| (ii) | 0.045 g (0.2 mmol) of HI in the form of an aqueous solution at a concentration of 57% (by weight); |
| (iii) | 0.5 g (28 mmol) of water; |
| (iv) | 2.0 g (20 mmol) of 3-pentenoic acid; |
| (v) | 10 cm$^3$ of acetic acid. |

The ampoule was placed in a 125-ml autoclave. The autoclave was closed hermetically, placed in an agitated oven and connected to the supply of gas under pressure. 2 bars of CO were introduced cold and the mixture was heated to 175° C. over 20 minutes. When this temperature was reached, the pressure was controlled at 20 bars.

After a reaction period of 20 minutes, the agitation and heating were stopped; the autoclave was then cooled and degassed.

The reaction solution was analyzed by gas phase chromatography and by high performance liquid chromatography.

The quantities of products formed (molar yield based on the 3-pentenoic acid connected) were as follows:

Valeric acid (Pa):  = 3.5%

4-Pentenoic acid (P4):  = 1%

3-Pentenoic acid (P3):  = 30%

2-Pentenoic acid (P2):  = 6.5%

γ-Valerolactone: 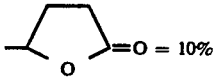 = 10%

Ethylsuccinic acid (A3): 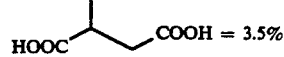 = 3.5%

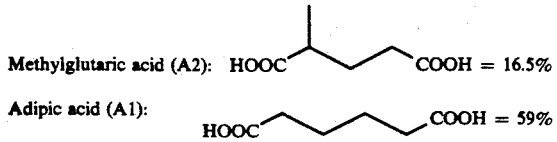

Methylglutaric acid (A2): HOOC...COOH = 16.5%

Adipic acid (A1): HOOC...COOH = 59%

The degree of linearity (L) was 75%. The degree of conversion of 3-pentenoic acid (DC) was 70%.

EXAMPLES 2 AND 3

A first series of experiments was carried out following the operating procedure of Example 1, only the quantity of HI charged being modified.

The particular reaction conditions and the results obtained, all parameters being otherwise the same, are reported in Table I below, in which the conventions employed are the same as in Example 1:

TABLE I

| Example | HI/Ir | DC % | A1 % | L % | M4L % |
| --- | --- | --- | --- | --- | --- |
| 2 | 1 | 36 | 49 | 65 | 10 |
| 1 | 2 | 70 | 59 | 75 | 10 |
| 3 | 3 | 50 | 48 | 70 | 20 |

EXAMPLE 4

The procedure of Example 3 was repeated following the operating procedure of Example 1, the quantity of iridium in the form of [IrCl(Cod)]₂ being reduced: 12.6 mg (0.0375 mmol), the quantities of the various other charges remaining the same.

The HI/Ir molar ratio was thus 8.

The reaction time at temperature was 60 minutes.

The results obtained are reported below (with the conventions employed being as in Example 1):

| DC of 3-pentenoic acid | 58% |
| --- | --- |
| A1 | 5% |
| L | 62% |
| M4L | 92% |

EXAMPLES 5 TO 12

A series of experiments was carried out in the autoclave and following the operating procedure described above on a charge containing:
(i) 0.1 mmol of iridium in the form of $Ir_4(CO)_{12}$;
(ii) 0.2 mmol of HI in the form of an aqueous solution at a concentration of 57% (by weight);
(iii) 20 mmol of 3-pentenoic acid;
(iv) a variable quantity of water;
(v) 10 cm³ of acetic acid.

The particular reaction conditions and the results obtained over 20 minutes of reaction at a temperature of 175° C. are reported in Table II below, in which P(CO) represents the partial pressure of carbon monoxide at temperature.

TABLE II

| Example | H₂O mmol | P (CO) bar | DC % | A1 % | L % | M4L % |
| --- | --- | --- | --- | --- | --- | --- |
| 5 | 17 | 20 | 60 | 62.5 | 78 | 10 |
| 6 | 29 | " | 70 | 65.5 | 81 | 8.5 |
| 7 | 67 | " | 37 | 41 | 72 | 24 |
| 8 | 193 | " | 34 | 40 | 67 | 20 |
| 9 | 29 | 5 | 51 | 21 | 72 | 6.5 |
| 10 | " | 10 | 82 | 63 | 84 | 10 |
| 11 | " | 15 | 68 | 63 | 81 | 10.5 |
| 12 | " | 50 | 57 | 59 | 78 | 10 |

EXAMPLE 13

The procedure of Example 6 was repeated, only the temperature being modified (190° C.).

The results obtained, all reaction conditions being otherwise the same, were as follows:
DC (%)=84
Al(%)=39
L(%)=76
M4L(%)=9

EXAMPLE 14

The procedure of Example 6 was repeated, only the quantity of iridium charged being modified (0.05 mmol).

The results obtained, all reaction conditions being otherwise the same, were as follows:
DC (%)=26
Al (%)=39
L (%)=63
M4L (%)=23

EXAMPLE 15

The procedure of Example 6 was repeated, the quantity of iridium charged being doubled.

The results obtained, all reaction conditions being otherwise the same, were as follows:
DC (%)=73
Al (%)=56
L (%)=82
M4L (%)=9

COMPARATIVE EXAMPLE

The procedure of Example 6 was repeated, but with the HI being replaced with an equivalent quantity of HBr.

The results obtained, all reaction conditions being otherwise the same, were as follows:
DC (%)=9
Al (%)=0
M4L (%)=83

EXAMPLES 16 AND 17

The procedure of Example 6 was repeated, only the nature of the pentenic acid charged being changed.

The particular reaction conditions and the results obtained, all parameters being otherwise the same, are reported in Table III below:

TABLE III

| Example | Acid Charged | DC % | A1 % | L % | M4L % | PA % |
| --- | --- | --- | --- | --- | --- | --- |
| 6 | 3-pentenoic | 70 | 65.5 | 81 | 8.5 | 3.5 |
| 16 | 4-pentenoic | 100 | 63 | 88 | 14.5 | 3 |
| 17 | 2-pentenoic | 45 | 54.5 | 88 | 6 | 24 |

EXAMPLE 18

The following materials were introduced into a glass ampoule purged beforehand with argon:

(i) 33.6 mg (0.1 mmol) of iridium in the form of [IrCl(Cod)]$_2$;
(ii) 0.045 g (0.2 mmol) of HI in the form of an aqueous solution at a concentration of 57% (by weight);
(iii) 0.5 g (29 mmol) of water;
(iv) 11.9 g (119 mmol) of 3-pentenoic acid.

The ampoule was placed in a 125-ml autoclave.

The autoclave was closed hermetically, placed in an agitated oven and connected to the supply of gas under pressure. 2 bars of CO were introduced cold and the mixture was heated to 175° C. over 20 minutes. When this temperature was reached, the pressure was controlled at 20 bars.

After a reaction time of 55 minutes, the agitation and heating were stopped and the reaction solution was analyzed as in Example 1.

The following results were obtained (with the conventions employed being as in Example 1):

| DC of 3-pentenoic acid | 34% |
|---|---|
| A1 | 71% |
| L | 86% |
| M4L | 11% |

EXAMPLE 19

The procedure of Example 1 was repeated with the following charges:
(i) 33.6 mg (0.1 mmol) of iridium in the form of [IrCl(Cod)]$_2$;
045 g (0.2 mmol) of HI in the form of an aqueous solution at a concentration of 57% (by weight);
(iii) 0.5 g (28 mmol) of water;
(iv) 2.0 g (2 mmol) of 3-pentenoic acid;
(v) 10 g of adipic acid.

The following results were obtained (with the conventions employed being as in Example 1):

| DC of 3-pentenoic acid | 95% |
|---|---|
| A1 (adipic acid formed, excluding the acid initially charged) | 77% |
| L | 86% |
| M4L | 12% |

EXAMPLE 20

The procedure of Example 18 was repeated With the following charges:
(i) 33.6 mg (0.1 mmol) of iridium in the form of [IrCl(Cod)]$_2$;
(ii) 0.045 g (0.2 mmol) of HI in the form of an aqueous solution at a concentration of 57% (by weight);
(iii) 0.5 g (28 mmol) of water;
(iv) 2.0 g (2 mmol) of 3-pentenoic acid;
(v) 10 g of 2-pentenoic acid.

The following results were obtained (with the conventions employed being as in Example 1):

| DC of 3-pentenic acid | 40% |
|---|---|
| A1 | 59% |
| L | 83% |
| M4L | 3% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of adipic acid, comprising reacting water and carbon monoxide with at least one pentenic acid, in the presence of a catalytically effective amount of an iridium-based catalyst and at least one iodine-containing promoter therefor, at an elevated temperature, at a pressure greater than atmospheric pressure, and in an at least one saturated aliphatic carboxylic acid, ethylenically unsaturated aliphatic carboxylic acid or aromatic carboxylic acid reaction medium having not more than 20 carbon atoms, with the I/Ir atomic ratio being less than 10.

2. The process as defined by claim 1, said at least one pentenic acid comprising 3-pentenoic acid, 2-pentenoic acid, 4-pentenoic acid or mixture thereof.

3. The process as defined by claim 1, wherein the water/pentenic acid(s) molar ratio is less than or equal to 10.

4. The process as defined by claim 1, said carboxylic acid reaction medium comprising a $C_2$-$C_6$ saturated aliphatic carboxylic acid.

5. The process as defined by claim 4, said carboxylic acid comprising acetic acid or adipic acid.

6. The process as defined by claim 1, said carboxylic acid reaction medium comprising 3-pentenoic acid, 2-pentenoic acid, 4-pentenoic acid or mixture thereof.

7. The process as defined by claim 1, said carboxylic acid reaction medium comprising at least 10% of the volume of the reaction mixture.

8. The process as defined by claim 7, said carboxylic acid reaction medium comprising from 10% to of the volume of the reaction mixture.

9. The process as defined by claim 1, wherein the concentration of iridium in the reaction mixture ranges from $10^{-4}$ to $10^{-1}$ mol/l.

10. The process as defined by claim 1, carried out at a temperature ranging from 100° to 240° C.

11. The process as defined by claim 1, carried out at a partial pressure of carbon monoxide ranging from 2 to 25 bars.

12. The process as defined by claim 1, wherein the I/Ir atomic ratio is higher than or equal to 0.1.

13. The process as defined by claim 12, said I/Ir atomic ratio ranging from 1 to 5.

14. The process as defined by claim 8, said carboxylic acid reaction medium comprising from 30% to 99% of the volume of the reaction mixture.

15. The process as defined by claim 10, carried out at a temperature ranging from 160° to 190° C.

16. The process as defined by claim 11, carried out at a partial pressure of carbon monoxide ranging from 5 to 100 bars.

* * * * *